(12) United States Patent
van der Avoort et al.

(10) Patent No.: US 9,778,238 B2
(45) Date of Patent: Oct. 3, 2017

(54) RESONANT CO2 SENSING WITH MITIGATION OF CROSS-SENSITIVITIES

(71) Applicant: ams International AG, Rapperswil (CH)

(72) Inventors: Casper van der Avoort, Eindhoven (NL); Willem Besling, Eindhoven (NL)

(73) Assignee: ams International AG, Rapperswil-Jona (CH)

( * ) Notice: Subject to any disclaimer, the term of this patent is extended or adjusted under 35 U.S.C. 154(b) by 157 days.

(21) Appl. No.: 14/480,986

(22) Filed: Sep. 9, 2014

(65) Prior Publication Data

US 2016/0069850 A1 Mar. 10, 2016

(51) Int. Cl.
*G01N 33/00* (2006.01)
*G01N 29/22* (2006.01)
(Continued)

(52) U.S. Cl.
CPC .......... *G01N 33/004* (2013.01); *G01L 9/0016* (2013.01); *G01N 29/022* (2013.01); *G01N 29/036* (2013.01); *G01N 29/222* (2013.01); *G01N 29/2406* (2013.01); *G01N 29/2431* (2013.01); *G01N 29/323* (2013.01); *G01N 29/4436* (2013.01); *G01N 33/0031* (2013.01);
(Continued)

(58) Field of Classification Search
CPC .......... G01N 9/04; G01N 9/266; G01N 29/32; G01N 29/323; G01N 2009/004
USPC ........................................................ 73/24.06
See application file for complete search history.

(56) References Cited

U.S. PATENT DOCUMENTS 5,645,071 A 7/1997 Harnoncourt et al.
7,047,810 B2 * 5/2006 Kogan .................... G01L 21/22
73/702

(Continued)

FOREIGN PATENT DOCUMENTS

EP 2700928 A2 2/2014
WO WO-2009071746 A1 6/2009

OTHER PUBLICATIONS

Humbert, A., et al. "A Lower Power CMOS Integrated Sensor for CO2 Detection in the Percentage Range", 978-1-4673-5983-2/13/ © 2013 IEEE, Transducers 2013, Barcelona, Spain, Jun. 16-20, 2013.

(Continued)

*Primary Examiner* — Justin Olamit
(74) *Attorney, Agent, or Firm* — McDermott Will & Emery LLP

(57) ABSTRACT

Various exemplary embodiments relate to a device to measure carbon dioxide ($CO_2$) levels, including a first oscillator group comprising a first sensor to measure air pressure, where the first sensor comprises a first sealed membrane, and where the first sealed membrane overlays a sealed first cavity; a second oscillator group including a second sensor to measure the resonance frequency of a second unsealed oscillating membrane, and where the second unsealed membrane overlays a second cavity in contact with the air outside of the second sensor; and a mixer accepting as input a first frequency measurement output from the first oscillator group and a second frequency measurement output from the second oscillator group, outputting the difference of the first frequency measurement and the second frequency measurement, and computing a carbon dioxide measurement based on the difference.

9 Claims, 6 Drawing Sheets

(51) Int. Cl.
*G01N 29/32* (2006.01)
*G01N 29/44* (2006.01)
*G01L 9/00* (2006.01)
*G01N 29/02* (2006.01)
*G01N 29/036* (2006.01)
*G01N 29/24* (2006.01)

(52) U.S. Cl.
CPC ............. *G01N 2291/021* (2013.01); *G01N 2291/0255* (2013.01); *G01N 2291/0256* (2013.01); *G01N 2291/02809* (2013.01); *G01N 2291/02818* (2013.01)

(56) References Cited

U.S. PATENT DOCUMENTS

| | | | |
|---|---|---|---|
| 7,273,763 B1* | 9/2007 | Neumeier | G01L 9/0042 438/51 |
| 8,256,298 B2 | 9/2012 | Suijlen et al. | |
| 8,413,517 B2* | 4/2013 | Janarthanam | H01M 8/04388 73/114.01 |
| 2002/0115198 A1 | 8/2002 | Nerenberg et al. | |
| 2004/0197227 A1 | 10/2004 | Hauan et al. | |
| 2005/0262943 A1 | 12/2005 | Claydon et al. | |
| 2010/0010750 A1 | 1/2010 | Baron et al. | |
| 2012/0006096 A1 | 1/2012 | Ackley et al. | |
| 2013/0192372 A1 | 8/2013 | Colinet et al. | |
| 2013/0233086 A1* | 9/2013 | Besling | G01L 9/0073 73/724 |
| 2014/0102172 A1 | 4/2014 | Daanen et al. | |

OTHER PUBLICATIONS

Matthijs, "Model-Based Design of MEMS Resonant Pressure Sensors", Aug. 29, 2011, 1-136.

M.A.G. Suijlen, et al., "Squeeze film damping in the free molecular flow regime with full thermal accommodation", Sensors and Actuators A: Physical Jan. 2009, pp. 171-179.

* cited by examiner

RESONANT CO2 SENSING WITH MITIGATION OF CROSS-SENSITIVITIES

TECHNICAL FIELD

Various exemplary embodiments disclosed herein relate generally to $CO_2$ sensing.

Electronic sensors may monitor air quality or gas composition in many ways; several physical properties of a gas mixture will change as the composition changes. For example, a sensor may be based on detecting the thermal conductivity of a gas mixture using a heated wire and measuring the heat dissipation of this wire to the surroundings.

Alternatively, a device may take advantage of the availability of accurate sensing of frequency by being sensitive to the average molar mass of a gas mixture, where the molar mass is reflected in the resonance frequency of the device. However, as for any gas sensor, the response will be varying with multiple influences, for example, gas pressure, temperature, and/or relative humidity. A molar mass sensor will also compensate for cross-sensitivities. Many methods require that the gas be in a particular state relative to the sensor, for example, a low vacuum or small space. Controlling the flow of gas in a detector may be difficult. At higher pressures and larger spaces (in the micro-meter range), molecules will collide with each other before hitting the sensor surface.

Specifically, $CO_2$ sensing may work in a number of ways. Two current methods include a material-based method where a material absorbs $CO_2$ and as a consequence changes electrical capacitance; and another where wire temperature is read by measuring electrical resistance—changes in the air mixture around a heated free-hanging wire result in changing the thermal conductivity of the medium, and hence the cooling of the heated wire. Another method is also known, resonant sensing of $CO_2$. Generally, this method requires a functional material on a MEMS element that resonates, detecting mass changes which result in frequency changes.

In ideal conditions, e.g. in the laboratory or other controlled conditions, there are several ways to measure the $CO_2$ content of a gas mixture. However, in the field, conditions are rarely ideal. For example, molar mass influences the average speed of particles (i.e., molecules in collision) in air. This in turn effects the collisions or impacts of particles on the walls (e.g., sensors) they encounter. The dynamic effects may be expressed as an air-film stiffness, as well as an air film damping constant. The quality factor or Q-factor, the measurement of the resonant system's relative bandwidth, affects the range in which a system can detect gasses—in order to be able to measure small frequency shifts it is important to have sufficiently high Q.

For example, in devices operating in a vacuum, resonance frequency can be determined with high resolution (sub-ppm accuracy in detection of frequency shift) using a resonator with Q=40000. However, Q drops significantly when changing the ambient from vacuum to regular air. In air, that same resonator may exhibit a Q=3900. With this resonator, 1 ppm-level frequency detection is possible. However, a pressure sensor membrane uses a different type of resonator (bending mode rather than bulk mode), and reaches suitable Q levels only in vacuum using a sealed membrane. Requiring a vacuum or other specific environmental variables in order to reach suitable Q levels may be impractical for use in real-world conditions for a host of reasons, not least because it may be necessary to detect changing conditions in open air.

An open structure has a resonance frequency that depends on gas pressure. However, the Q level at ambient pressure may be around 200 due to damping losses in air (due to air viscosity). Even with Q=200, frequency resolution allows detection of 20 ppm relative shift in resonance frequency. However, this means that in ambient conditions, a $CO_2$ change of 200 ppm particles results in a 12 ppm frequency change, which is already close to this detection limit of current devices. With oxygen and nitrogen as major components, the influence in the change of concentration of any of the other gases means that only small changes are to be expected in the molar mass. It is desired to be able to detect frequency shifts of the order of 10s of ppms, that is, when only the $CO_2$ concentration would have an effect on frequency.

SUMMARY

In light of the present desire for frequency-based $CO_2$ sensing, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various exemplary embodiments relate to the frequency shift of an oscillating membrane in relation to the amount of $CO_2$ molecules in the air around the membrane. The frequency shift may be proportional to temperature, pressure and humidity fluctuations in the air. In some embodiments, the resonant $CO_2$ sensor may function as an add-on to a combination of sensors for temperature, humidity and pressure. Various exemplary embodiments disclosed herein relate generally to a method to overcome cross-sensitivity to relative humidity.

Various exemplary embodiments relate to a device to measure carbon dioxide ($CO_2$) levels, including a first oscillator group comprising a first sensor to measure air pressure, wherein the first sensor includes a first sealed membrane, wherein the first sealed membrane overlays a sealed first cavity; a second oscillator group including a second sensor to measure the resonance frequency of a second unsealed oscillating membrane, wherein the second unsealed membrane overlays a second cavity in contact with the air outside of the second sensor; and a mixer accepting as input a first frequency measurement output from the first oscillator group and a second frequency measurement output from the second oscillator group, outputting the difference of the first frequency measurement and the second frequency measurement; and a circuit accepting as input the difference and outputting a carbon dioxide measurement. In various alternate embodiments, the first membrane and the second membrane are identical in size, shape, and manufacturing process. In various embodiments, the first membrane and the second membrane measure 200×200 µm2. In alternate embodiments, the first sealed membrane is hermetically sealed and deflects under a pressure gradient. In some alternate embodiments, deflecting under a pressure gradient includes deflecting under a pressure difference between inside the membrane and outside the membrane. In some alternate embodiments, the second oscillator group further includes a first top electrode and a second bottom electrode.

Various exemplary embodiments relate to a device to measure carbon dioxide ($CO_2$) levels, including a first sensor to measure air pressure, wherein the first sensor includes a sealed membrane, wherein the sealed membrane overlays a sealed first cavity; a second sensor to measure the resonance frequency of an unsealed oscillating membrane, wherein the second sensor comprises a heater, wherein the unsealed membrane overlays a second cavity in contact with the air outside of the second sensor, and wherein the heater is in contact with the interior surface of the second cavity; and a mixer accepting as input a first frequency measurement output from the first sensor and a second frequency measurement output from the second sensor, and outputting the difference of the first frequency measurement and the second frequency measurement; and a circuit accepting as input the difference and outputting a carbon dioxide measurement. In various alternate embodiments, the first membrane and the second membrane are identical in size, shape, and manufacturing process. In various embodiments, the first membrane and the second membrane measure 200×200 µm2. In alternate embodiments, the first sealed membrane is hermetically sealed and deflects under a pressure gradient. In some alternate embodiments, the second oscillator group further includes a first top electrode and a second bottom electrode.

Various exemplary embodiments relate to a tangible and non-transitory machine-readable storage medium encoded with instructions thereon for execution by a device for measuring carbon dioxide ($CO_2$) levels, wherein said tangible and non-transitory machine-readable storage medium includes instructions for taking a first air pressure measurement using a first sensor, wherein the first sensor includes a sealed membrane; instructions for taking a second resonance frequency of air measurement using a second sensor, wherein the second sensor includes an unsealed oscillating membrane, wherein the unsealed membrane overlays a first cavity in contact with the air outside of the second sensor; instructions for computing a difference of the first frequency measurement and the second frequency measurement; and instructions for computing a carbon dioxide measurement based on the difference. Alternative embodiments include instructions for, just before measuring the resonance frequency of air using the second sensor, heating the second cavity; and instructions for reading the temperature of the first membrane. In some embodiments, instructions for taking a second resonance frequency of air measurement using a second sensor further include instructions for initiating electrostatic mechanical actuation of a top electrode of the device. In other embodiments, electrostatic mechanical actuation of a top electrode further includes applying a DC plus AC voltage over two electrodes of the device.

Various exemplary embodiments relate to a method of measuring carbon dioxide ($CO_2$) levels, the method including taking a first air pressure measurement using a first sensor, wherein the first sensor includes a sealed membrane; taking a second resonance frequency of air measurement using a second sensor, wherein the second sensor includes an unsealed oscillating membrane, wherein the unsealed membrane overlays a first cavity in contact with the air outside of the second sensor; computing the difference of the first frequency measurement and the second frequency measurement; and computing a carbon dioxide measurement based on the difference. Various exemplary methods further include, just before measuring the resonance frequency of air using the second sensor, heating the second cavity; and reading the temperature of the first membrane. In various alternative embodiments, the step of taking a second resonance frequency of air measurement using a second sensor further includes electrostatic mechanical actuation of a top electrode. In various exemplary embodiments, electrostatic mechanical actuation of a top electrode further includes applying a DC plus AC voltage over two electrodes.

It should be apparent that, in this manner, various exemplary embodiments enable $CO_2$ sensing.

BRIEF DESCRIPTION OF THE DRAWINGS

In order to better understand various exemplary embodiments, reference is made to the accompanying drawings, wherein.

DETAILED DESCRIPTION

Figure 1:
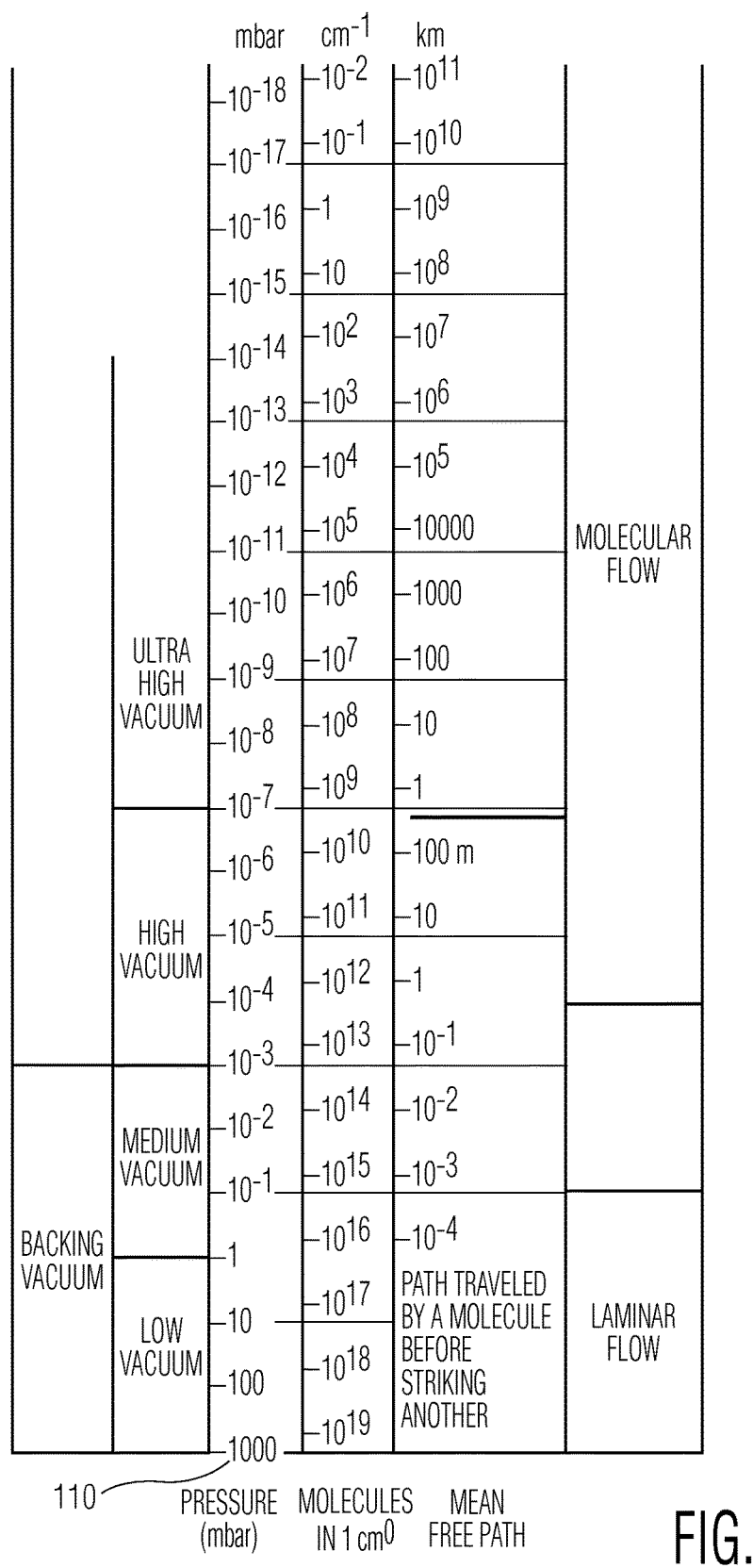
FIG. 1 provides a chart illustrating the distinction between viscous laminar flow and free molecular flow with regards to the expected path traveled by a molecule before striking another molecule.

In view of the foregoing, it would be desirable to implement a device to measure $CO_2$ content in air that does not rely on any specific pressure, temperature, or humidity. Only a change in molar mass of the gas mixture is detected. In particular, it would be desirable to create a method to separate the desired signal from other ambient parameters.

As for any gas sensor, measurements will vary due to multiple influences, for example, gas pressure, temperature, and relative humidity. These cross-sensitivities may be mitigated to achieve detection of $CO_2$ ppm level fluctuations in ambient air in the order of 200 ppm.

Referring now to the drawings, in which like numerals refer to like components or steps, there are disclosed broad aspects of various exemplary embodiments.

FIG. 1 illustrates the distinction between viscous laminar flow and free molecular flow with regards to the expected path traveled by a molecule before striking another molecule. When gas is in a state of free molecular flow, the mean free path of molecules is larger than the largest volume dimension of the encapsulation around the gas. One expected result is that molecules collide with the walls, not with each other. Such a state corresponds to low vacuum and/or small distance between the walls in which the gas is enclosed. At regular air pressures, gas acts in a state of viscous (laminar) flow.

At higher pressures (leftmost region of FIG. 1, 110) molecules will collide with each other before hitting a wall or other surface such as a sensor surface. On a crude scale, illustrated in FIG. 1, the free path length at the assumed standard sea level pressure of 1000 mbar is approximately 100 nm.

In the micro-meter range of free path length, such as that separating the walls in the micro structure of a detector, a molecular flow up to a level of above ~20 mbar would be expected. Note that in a gap of around 1 um the molecules will not travel collision-free from one surface to another, but will experience only a handful of collisions. Therefore, for gaps of around 1 um, a measurement of the mean velocities of molecules may be sufficiently accurate to be valuable. Although the gap height may be reduced to the mean free path length of molecules in ambient air conditions (i.e. ~100 nm), this may pose further constraints on manufacturing process control.

Figure 2A:
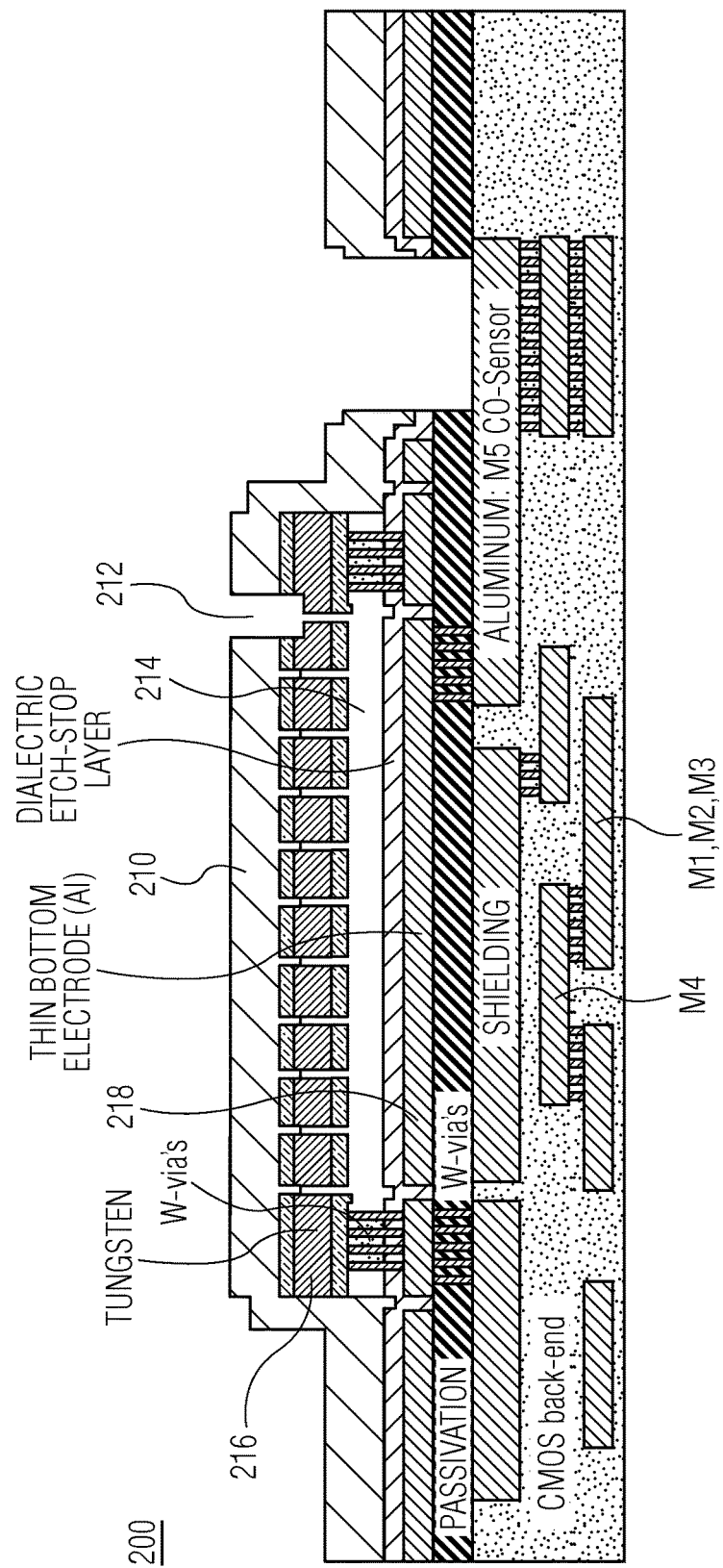
FIG. 2A illustrates an exemplary gas sensor open to the air.
Figure 2B:
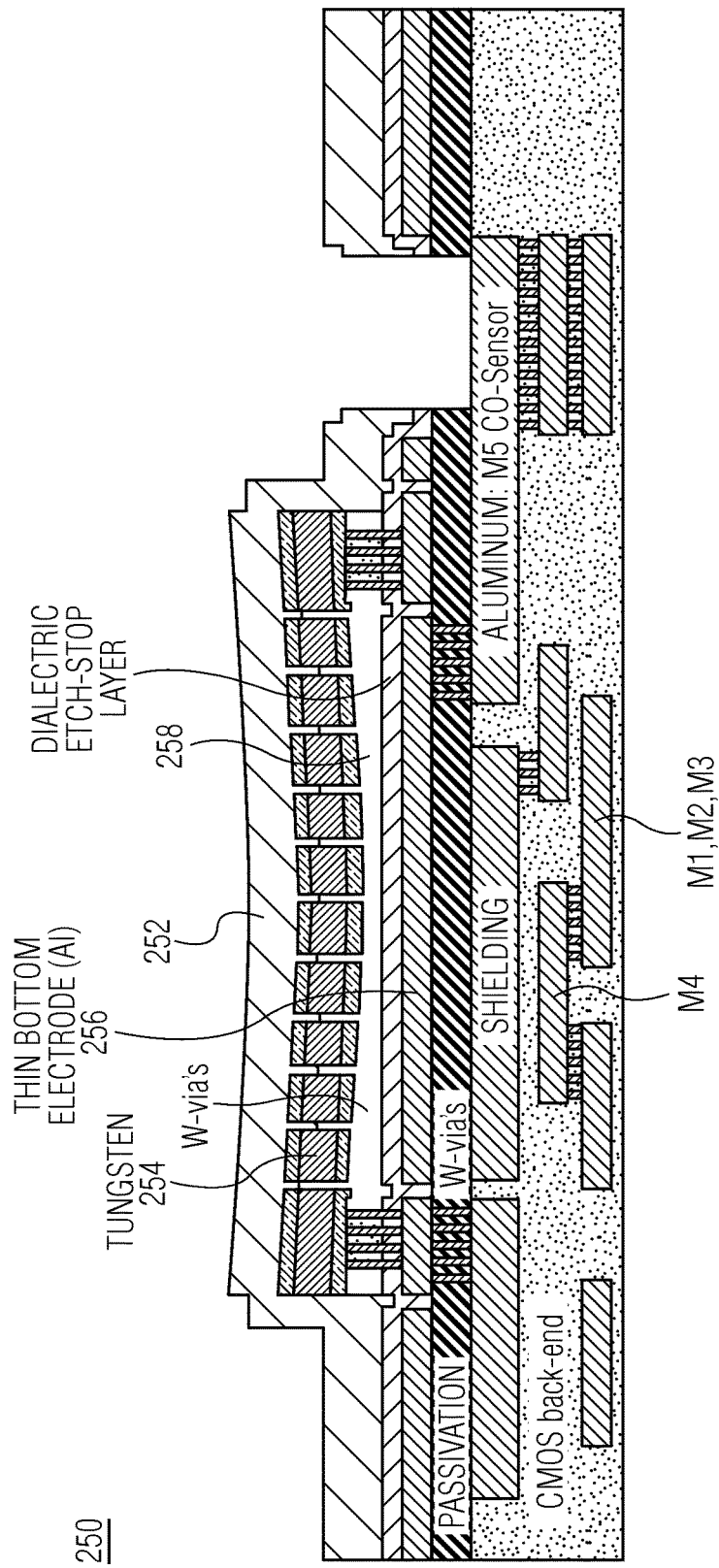
FIG. 2B illustrates an exemplary sealed air pressure sensor.

FIG. 2A illustrates an exemplary gas sensor 200 open to the air, in which the membrane 210 is in contact with the air through a gap 212 in the membrane 210, and thus is not deflected by an externally applied air pressure. FIG. 2B illustrates an exemplary sealed air pressure sensor 250, where the membrane 252 is hermetically sealed and deflects under a pressure difference between inside the membrane (in the sealed cavity 258) and outside the membrane. In the exemplary sealed pressure sensor arrangement of FIG. 2B, the electrical capacitance of a capacitor comprising a top-electrode 254, which may include tungsten (W), and a bottom electrode 256, which may include aluminum (Al), is a function of deflection of the top electrode, which in turn is a function of the pressure difference between inside and outside.

However, in order to detect ambient gases such as $CO_2$, the open structure illustrated in FIG. 2A is necessary so that ambient molecules can be detected after they pass through the gap of the sensor structure 212, such that the micro cavity 214 is in contact with the ambient air. In such an arrangement, dynamic aspects of the thin film of air in the micro cavity 214 can be probed and measured by electrostatic mechanical actuation of the top electrode. Electrostatic mechanical actuation may be achieved by applying a DC plus AC voltage over the two electrodes 216, 218.

Figure 3:
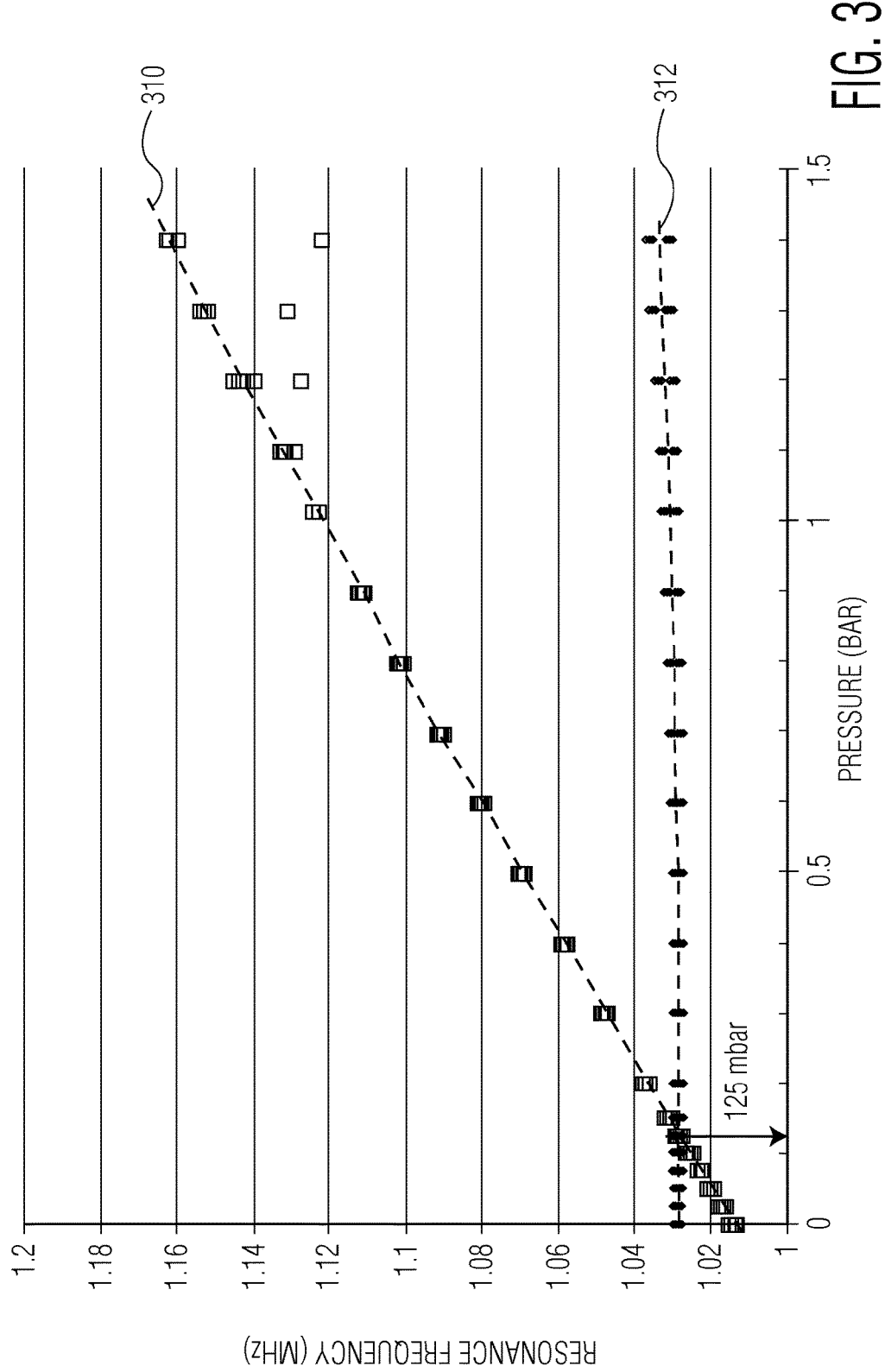
FIG. 3 illustrates resonance frequency measurements for exemplary open and closed sensors.

At the micro-meter range, the behavior of molecules at low pressures may be equal to that at higher pressure—transition from free molecular to viscous flow may not be visible. Thus, at a small scale it may not be necessary to take measurements under a vacuum in order to achieve proper measurements. FIG. 3 illustrates resonance frequency measurements for exemplary 200×200 $\mu m^2$ open and closed sensors 216, 218, 254, 256, as illustrated in FIGS. 2A and 2B where a micro cavity 214, 258 measures 0.6 micron high.

Data for the open structure of FIG. 2A along line 310 illustrates measurement of the resonance frequency of the top electrode 210 as a function of the air pressure. Because the membrane 210 of sensor 200 is open at gap 212, the pressure inside the cavity 214 is the same as the ambient pressure outside sensor 200, which is shown in FIG. 3 at varied levels in a range from 1 to over 1400 mbar.

As can be seen in FIG. 3, the resonance frequency of the membrane interacting with the air cavity below it measured by open sensor 200 depends on gas pressure, such that $$\omega^2 = \frac{k_{\it eff} + k_{\it film}}{m_{\it eff}} \text{ and}$$

$$k\_film = \frac{cAp}{d}$$

where $k_{film}$ equals air film stiffness, $k_{eff}$ equals mechanical stiffness, $m_{eff}$ equals the effective mass; and k_film includes a gas-type-dependent constant c, the frontal area A, pressure p and electrode separation d. The square-root nature in frequency is not visible in the pressure range of FIG. 3. The slope of the frequency-vs-pressure line is proportional to the molar mass of the gas mixture. Therefore, the measurements of sensor 216 may be assumed to be at nominal regular air pressure of approximately 1000 mbar, and then combined with the measurement of the real pressure—when the average pressure is known, the absolute resonance frequency of the gas sensor may be used to determine the molar mass of the measured gas.

The next calculation indicates what the change in frequency to be detected should be, in order to see a change of 200 ppm CO2. Gas film stiffness and gas film damping coefficient may be determined as a function of pressure for different gases, for example, helium (M=4), nitrogen (M=28) and hexafluoroethane (M=138). Squeeze film damping is also a function of the gas-type, but air film stiffness and hence the $k_{film}$-vs-p ratio scales with M. In fact, it scales as $\sqrt{M}$, meaning relative slopes of 2, 5.3, and 12 for a plot of the $k_{film}$-vs-p ratios of helium, nitrogen, and hexafluoroethane when taken at very low pressures, for example, between 0 and 1 mbar.

The major components of regular air are Oxygen, Nitrogen, Carbon Dioxide, Hydrogen, Argon, Neon, Helium, Krypton, and Xenon (water vapor, especially in the form of humidity, is also a component of ambient air, but is discussed later). The following table (Table 1) illustrates a change in average molar mass for the major components, summing to an indicated overall molar mass (28.971), and their molar distribution; due to rounding, one million plus 2 parts per million are listed (note that $CO_2$ is assumed to have 303 ppm in this mixture):

TABLE 1

| Gas | Volume Fraction | Mass Fraction | Molar Mass | Symbol | Partial Mass | Mol | ppm |
|---|---|---|---|---|---|---|---|
| Oxygen | 20.95 | 23.2 | 32 | $O_2$ | 6.704 | 0.725 | 210048 |
| Nitrogen | 78.09 | 75.47 | 28.02 | $N_2$ | 21.881 | 2.693433262 | 780343 |
| Carbon Dioxide | 0.03 | 0.046 | 44.01 | $CO_2$ | 0.013 | 0.001045217 | 303 |
| Hydrogen | 0.00005 | ~0 | 2.02 | $H_2$ | 0.000 | | |
| Argon | 0.933 | 1.28 | 39.94 | Ar | 0.373 | 0.032048072 | 9285 |
| Neon | 0.0018 | 0.0012 | 20.18 | Ne | 0.000 | 5.94648E−05 | 17 |
| Helium | 0.0005 | 0.00007 | 4 | He | 0.000 | 0.0000175 | 5 |
| Krypton | 0.0001 | 0.0003 | 83.8 | Kr | 0.000 | 3.57995E−06 | 1 |
| Xenon | 9(10$^{-6}$) | 0.00004 | 131.29 | Xe | | 3.04669E−07 | 0 |
| | | | | SUM: | 28.971 | | 1000002 |

With oxygen and nitrogen as major components, the influence in the change of concentration of any of the other gases means that only small changes are to be expected in the molar mass. For example, where $CO_2$ is 303 ppm as demonstrated in Table 1, molar mass M=28.971. Table 2 illustrates a change in the CO2-level, while keeping the total amount of particles constant:

TABLE 2

| Gas | Partial Mass | Mol | ppm | increased CO$_2$ | CO$_2$ DELTA | Partial Mass |
|---|---|---|---|---|---|---|
| Oxygen | 6.704 | 0.725 | 210048 | 210006 | | 6.72 |
| Nitrogen | 21.881 | 2.693433262 | 780343 | 780190 | | 21.861 |
| Carbon Dioxide | 0.013 | 0.001045217 | 303 | 500 | 197 | 0.022 |
| Hydrogen | 0.000 | | | | | 0 |
| Argon | 0.373 | 0.032048072 | 9285 | 9283 | | 0.371 |
| Neon | 0.000 | 5.94648E−05 | 17 | 17 | | 0 |
| Helium | 0.000 | 0.0000175 | 5 | 5 | | 0 |
| Krypton | 0.000 | 3.57995E−06 | 1 | 1 | | 0 |
| Xenon | | 3.04669E−07 | 0 | 0 | | |
| SUM: | 28.971 | | 1000002 | 1000002 | | 28.974 |

As is shown, changing the CO2 concentration from 303 ppm to 500 ppm, a difference of 197 ppm, while assuming proportional accommodation by all other gases, results in a new molar mass. This is a worst-case estimate of the to-be-detected mass change, because actually it is more likely that O$_2$ will be traded for CO$_2$ by breathing, and N$_2$ will remain unaffected, resulting in a slightly more pronounced change in molar mass. In the exemplary situation shown in Table 2, the relative change is 0.011% or 110 ppm, and the new molar mass M=28.974. Although this is a minute difference, a measurement made before and after the change at exactly the same pressure level would result in a noticeable change in frequency.

A change in molar mass reflects a change in the spring constant of the air film as reflected by the equation $$\omega^2 = \frac{k_{eff} + k_{film}}{m_{eff}}.$$

Figure 4:
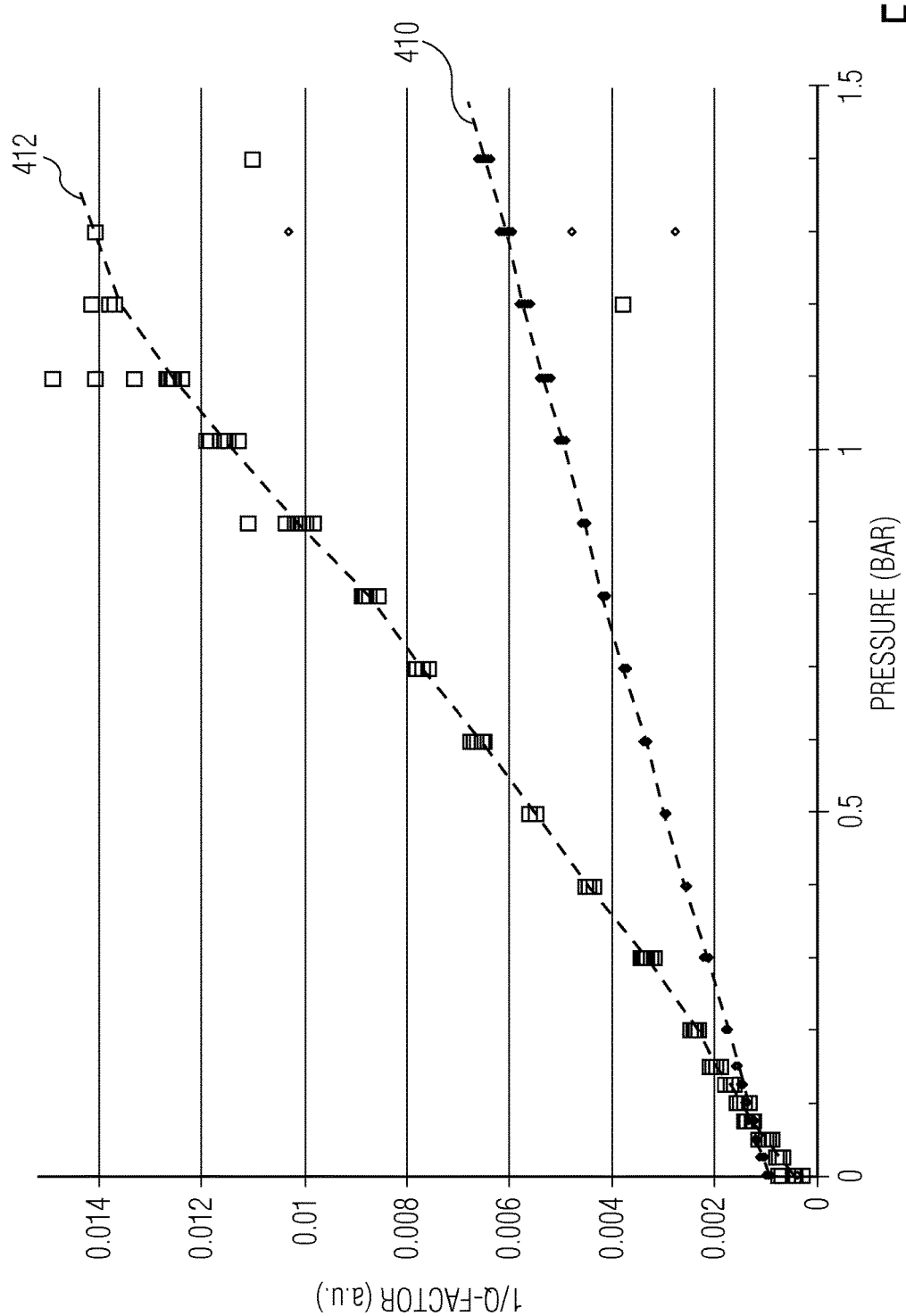
FIG. 4 illustrates the relation between damping versus pressure for open and sealed devices.

This value may be derived from a reading by the sensor 216 of frequency f, where f=√ω. For example, for a 240 micron square membrane 210 shown in the configuration of open sensor 200 in FIG. 2A, $k_{eff}$=1.3*10$^4$ [N/m]. At 1 bar the airfilm has $k_{film}$=3.6*10$^3$ [N/m]. With effective mass $m_{eff}$=5.5*10$^{-10}$ [kg], the resonance frequency for this exemplary device is $f_{res}$=omega/2pi=874 kHz. If the molar mass of the gas mixture were to change, the ratio of $k_{film}$-vs-p will change and hence the airfilm stiffness at one bar will be different. (See, e.g., Matthijs Suijlen, "Model-based design of MEMS resonant pressure sensors", NXP 2011, Thesis. http://alexandria.tue.nl/extra2/716458.pdf, last accessed Aug. 14, 2014; esp. FIG. 4 (experiments where gas film stiffness and gas film damping coefficient are determined as a function of pressure, for different gases, with measurements only up to 1 mbar, residing in the regime of free molecular flow)). The proportional change on $k_{film}$ is 110 ppm, so the frequency with the above example will change from 874.000 kHz to 874.010 kHz, a change of 12 ppm.

FIG. 4 illustrates the relation between damping versus pressure for open and sealed devices such as sensors 200 and 250. As noted above, the Q factor affects the range in which a system can detect gasses—in order to be able to measure small frequency shifts it is important to have sufficiently high Q, but a pressure sensor membrane reaches suitable Q levels only in vacuum using a sealed membrane. As shown in FIG. 4, for pressure sensors with a sealed membrane, the Q factor (shown as damping factor 1/Q) is impacted by the outside pressure, as shown by line 410, but the frequency is nearly unchanged as a function of pressure as shown by line 312 in FIG. 3. Hence, there is no additional spring constant for sealed devices such as sensor 250. However, open devices such as gas sensor 200 have a significantly higher frequency and a lower Q of ~200 due to the squeezed film effect of air that is present/entrapped in the cavity 214 (as shown by line 412). As shown in FIG. 4, for both open and closed devices 1/Q is a linear function of pressure. The difference between the slope of the 1/Q curves 410, 412, is proportional to the additional damping effect of the air molecules that are present in the cavity.

Air pressure, temperature, and humidity all will change the detectable resonance frequency. In order to detect frequency shifts on the order of 10 ppms when only CO$_2$ concentration would have an effect on frequency, the effects of these factors should be mitigated. A sensor such as exemplary sensor 200 may be modified to mitigate these factors and achieve conditions in which it is possible to measure smaller frequency shifts than would be possible when measuring unaltered outside air.

For example, if the membranes 210, 252 incorporated into gas sensor 200 and pressure sensor 250 may be well matched, e.g. identical except for the difference of being sealed or unsealed, in order that the measurements from them would be under near-identical external conditions. In such an arrangement, the pressure effect on the resonance frequency of the open membrane 210 may be compensated for with the sealed membrane 252 acting as an absolute pressure sensor 250 relative to the open sensor 200.

Also, note that temperature effects will have the same delta on membranes 210 and 252—the difference signal will be much less depending on temperature (T). The delta in residual frequency $f_{res}$ between open and sealed membranes 210, 252 is a good measure to determine the changes in $f_{res}$ of the open membrane 210 because the effect of temperature variations will become small. As the resonance frequency of the sealed membrane 252 is not a function of pressure due to the fact that the cavity pressure is very low (as shown in FIG. 3) the actual slope of $f_{res}$ (P) is directly proportional to the molar density of the gas that is present inside the cavity 214. In order to detect a molar density change due to a gas composition variation of 200 ppm the error in the pressure measurement should be much smaller than 200 ppm. Currently known capacitive pressure sensors can achieve a relative accuracy of 2 Pa on 1 bar, or 20 ppm. The information on the Q-factor can also be used to extract information on damping which is dependent upon pressure and molecule mass.

Additionally, a method of mitigating moisture and humidity that may affect CO$_2$ detection is discussed below with relation to humidity effects and mitigation.

Because cross-sensitivities such as air pressure, temperature, and humidity determine the accuracy of the sensor, a system allowing the comparison of the resonance frequency of ambient gas and the degree of pressure to a significant degree of accuracy requires measurements from both an open-structure sensor and a sealed-membrane sensor, taken simultaneously.

Figure 5:
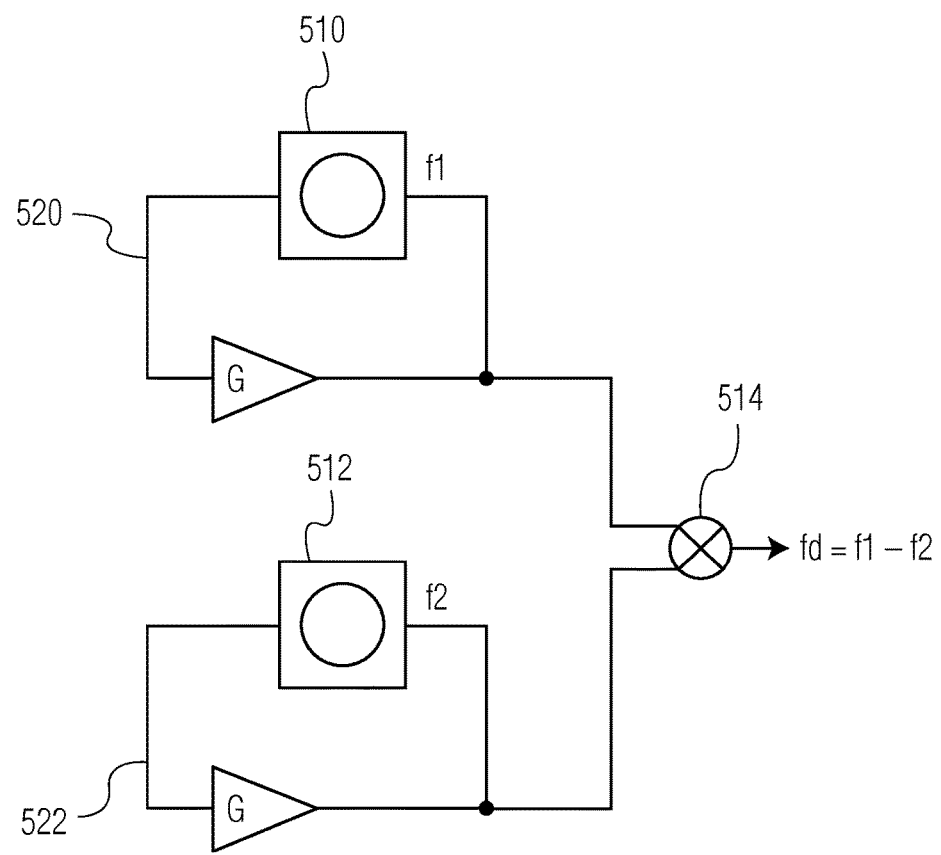
FIG. 5 illustrates an exemplary system for combining the measurements of two sensors.

To discriminate the effect of gas-mixture-change from changes in pressure or temperature, a difference in frequencies may be detected as illustrated in FIG. 5, where a system combines the measurements of the sensors such as, for example, sensors 200 and 250. Two sensor membranes 510 and 512 are incorporated in two separate oscillator loops 520, 522. The resulting frequencies f1 (of the pressure sensor) and f2 (of the gas or $CO_2$ sensor) are fed to a mixer 514, yielding the difference frequency fd. As illustrated in Tables 1 and 2 and FIGS. 3 and 4, the difference frequency fd at constant pressure is proportional to change in $CO_2$. At changing pressure levels, detected by f1, a stored look-up table may be generated by an initial calibration procedure to set a reference point for the value of f2 at a defined CO2 level.

As noted above, ambient air contains water molecules. Water vapor accounts for a significant number of molecules in the air. The molar mass of water is 18, compared to 44 for $CO_2$. The levels of water vapor tend to be very large compared to the few hundred ppm $CO_2$ that might be necessary to detect in many applications, e.g. in a $CO_2$ detector meant to warn humans of rising $CO_2$ levels before they become toxic. For example, Table 3 lists the ppm of water with varying relative humidity at room temperature and ~1 bar pressure:

TABLE 3

| Kelvin | Celsius | mbar | RH % | ppm |
|---|---|---|---|---|
| 298.15 | 25 | 1013.25 | 50 | 15619 |
| 298.15 | 25 | 1013.25 | 60 | 18743 |
| 298.15 | 25 | 1013.25 | 70 | 21867 |
| 298.15 | 25 | 1013.25 | 80 | 24990 |

The water content is also a strong function of temperature. For example, in Table 4, only temperature is varied:

TABLE 4

| Kelvin | Celsius | mbar | RH | ppm |
|---|---|---|---|---|
| 298.15 | 25 | 1013.25 | 50 | 15619 |
| 323.15 | 50 | 1013.25 | 50 | 60861 |
| 348.15 | 75 | 1013.25 | 50 | 190180 |
| 373.15 | 100 | 1013.25 | 50 | 499820 |

While the ppm-versus-RH % is nearly linear, the curve of ppm-versus-temperature shows an exponential nature. At very high levels of RH % the water content expressed in ppm approaches 30000 for the condition of room temperature and 1 bar air pressure. If the gas mixture in cavity 214 includes an applied temperature well, the ppm-level of water in air may be modulated by modulating the temperature of the sensor. A heater such as a joule heater may be incorporated in the structure of gas sensor 200 close to or in contact with cavity 214, in order to evaporate all moisture that is adsorbed onto the membrane 210 just before measuring the resonance frequency.

As discussed above, the gas sensor 200 senses the molar mass of a gas mixture (i.e. air) in a shallow cavity 214. The molar mass is reflected in the resonance frequency. The frequency also depends on temperature, RH % and pressure, so separate sensors are used to measure these parameters. To remove the combined cross-sensitivity of water and temperature, the system may use a modulation method where the temperature, and hence the water content, is cycled using a heater. Note that the absolute water concentration in the air is not directly modulated by the increasing temperature if there is no direct (e.g., liquid) water source—however, if the water film is evaporated from the surface inside the cavity the concentration of the water vapor molecules will increase. The frequency of the sensor will follow the temperature modulation because of its own temperature dependency, in addition to an even larger magnitude of the induced change in molar mass because of the fluctuating water levels. However, these effects can be compensated for by using the difference frequency of the sealed and open membranes in sensors 200, 250. The temperature modulation will cause the absolute humidity level to be changed while the $CO_2$ ppm-level remains constant.

According to the foregoing, various exemplary embodiments provide for compensating for cross-sensitivities related to a gas sensor. In particular, by implementing a multiple-sensor package, including a heater, and accounting for known effects.

It should be apparent from the foregoing description that various exemplary embodiments of the invention may be implemented in hardware and/or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principals of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A device to output a difference of frequency measurements, comprising:
   a first oscillator group comprising a first sensor to measure air pressure, wherein the first sensor comprises a first sealed membrane, wherein the first sealed membrane overlays a sealed first cavity;
   a second oscillator group comprising a second sensor to measure the resonance frequency of a second unsealed oscillating membrane, wherein the second unsealed membrane overlays a second cavity in contact with the air outside of the second sensor; and a mixer accepting as input a first frequency measurement output from the first oscillator group and a second frequency measurement output from the second oscillator group, and outputting a difference of the first frequency measurement and the second frequency measurement.

2. The device of claim 1, wherein the first sealed membrane and the second unsealed oscillating membrane measure 200×200 μm$^2$.

3. The device of claim 1, wherein the first sealed membrane is hermetically sealed and deflects under a pressure gradient.

4. The device of claim 3, wherein deflecting under a pressure gradient comprises deflecting under a pressure difference between inside the membrane and outside the membrane.

5. The device of claim 1, wherein the second oscillator group further comprises a first top electrode and a second bottom electrode.

6. A device to output a difference of frequency measurements, comprising:

a first sensor to measure air pressure, wherein the first sensor comprises a sealed membrane, wherein the sealed membrane overlays a sealed first cavity;

a second sensor to measure the resonance frequency of an unsealed oscillating membrane, wherein the second sensor comprises a heater, wherein the unsealed membrane overlays a second cavity in contact with the air outside of the second sensor, and wherein the heater is in contact with the interior surface of the second cavity; and a mixer accepting as input a first frequency measurement output from the first sensor and a second frequency measurement output from the second sensor, and outputting a difference of the first frequency measurement and the second frequency measurement.

7. The device of claim 6, wherein the sealed membrane and the unsealed oscillating membrane measure 200×200 μm$^2$.

8. The device of claim 6, wherein the sealed membrane is hermetically sealed and deflects under a pressure gradient.

9. The device of claim 6, wherein the second sensor further comprises a first top electrode and a second bottom electrode.

* * * * *